US00PP33065P2

(12) United States Plant Patent
Misato

(10) Patent No.: US PP33,065 P2
(45) Date of Patent: May 11, 2021

(54) ***SENECIO* PLANT NAMED 'SUNSENEHAHA'**

(50) Latin Name: *Senecio cruentus*
Varietal Denomination: Sunsenehaha

(71) Applicant: Tomoya Misato, Shiga (JP)

(72) Inventor: Tomoya Misato, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 16/974,013

(22) Filed: Sep. 5, 2020

(51) Int. Cl.
*A01H 5/02* (2018.01)
*A01H 6/14* (2018.01)

(52) U.S. Cl.
USPC ..... Plt./480
CPC ..... *A01H 6/14* (2018.05)

(58) Field of Classification Search
USPC ..... Plt./480
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Senecio* plant named 'Sunsenehaha', characterized by its upright and uniformly mounded plant habit; vigorous growth habit; freely branching habit; freely flowering habit; and daisy-type inflorescences with ray florets that are dark violet in color and disc florets that are dark purple in color.

1 Drawing Sheet

Botanical designation: *Senecio cruentus.*
Cultivar denomination: 'SUNSENEHAHA'.

BACKGROUND OF THE INVENTION

The present invention relates to a new and distinct cultivar of *Senecio* plant, botanically known as *Senecio cruentus*, and hereinafter referred to by the name 'Sunsenehaha'.

The new *Senecio* plant is a product of a planned breeding program conducted by the Inventor in Higashiomi, Shiga, Japan. The objective of the breeding program is to create new upright, uniformly mounding and vigorous *Senecio* plants with a freely-branching habit, early flowering and numerous attractive inflorescences.

The new *Senecio* plant originated from a cross pollination conducted by the Inventor in March, 2008 of a proprietary selection of *Senecio cruentus* identified as code number 326, not patented, as the female, or seed, parent with a proprietary selection of *Senecio cruentus* identified as code number KW74, not patented, as the male, or pollen, parent. The new *Senecio* plant was discovered and selected by the Inventor as a single flowering plant within the progeny of the stated cross-pollination in a controlled greenhouse environment in Higashiomi, Shiga, Japan in February, 2009.

Asexual reproduction of the new *Senecio* plant by terminal cuttings in a controlled greenhouse environment in Higashiomi, Shiga, Japan since October, 2009 has shown that the unique features of this new *Senecio* plant are stable and reproduced true to type in successive generations.

SUMMARY OF THE INVENTION

Plants of the new *Senecio* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Sunsenehaha'. These characteristics in combination distinguish 'Sunsenehaha' as a new and distinct *Senecio* plant:

1. Upright and uniformly mounded plant habit.
2. Vigorous growth habit.
3. Freely branching habit.
4. Freely flowering habit.
5. Daisy-type inflorescences with ray florets that are dark violet in color and disc florets that are dark purple in color.

Plants of the new *Senecio* can be compared to plants of the female parent selection. Plants of the new *Senecio* differ primarily from plants of the female parent selection in ray floret color as plants of the new *Senecio* have dark violet-colored ray florets whereas plants of the female parent selection have purple-colored ray florets.

Plants of the new *Senecio* can be compared to plants of the male parent selection. Plants of the new *Senecio* differ primarily from plants of the male parent selection in leaf shape as leaves of plants of the new *Senecio* have more shallow lobing than leaves of plants of the male parent selection.

Plants of the new *Senecio* can also be compared to plants of *Senecio cruentus* 'Sunsenebu', disclosed in U.S. Plant Pat. No. 12,104. In side-by-side comparisons, plants of the new *Senecio* differ from plants of 'Sunsenebu' in the following characteristics:

1. Plants of the new *Senecio* are more compact than plants of 'Sunsenebu'.
2. Leaves of plants of the new *Senecio* have more shallow lobing than leaves of plants of 'Sunsenebu'.
3. Leaves of plants of the new *Senecio* are darker green in color than leaves of plants of 'Sunsenebu'.
4. Plants of the new *Senecio* have smaller inflorescences than plants of 'Sunsenebu'.

5. Inflorescences of plants of the new *Senecio* are more upright than and not as reflexed as inflorescences of plants of 'Sunsenebu'.
6. Plants of the new *Senecio* and 'Sunsenebu' differ in ray floret color as plants of the new *Senecio* have darker violet-colored ray florets than plants of 'Sunsenebu'.
7. Plants of the new *Senecio* have longer phyllaries than plants of 'Sunsenebu'.
8. Plants of the new *Senecio* have longer peduncles than plants of 'Sunsenebu'.

BRIEF DESCRIPTION OF THE PHOTOGRAPHS

The accompanying photographs illustrate the overall appearance of the new *Senecio* plant showing the colors as true as it is reasonably possible to obtain in colored reproductions of this type. Colors in the photographs may differ slightly from the color values cited in the detailed botanical description which accurately describe the colors of the new *Senecio* plant. The photograph at the top of the sheet is a side perspective view of a typical flowering plant of 'Sunsenehaha' grown in a container. The photograph at the bottom of the sheet is a close-up view of a typical flowering plant of 'Sunsenehaha'.

DETAILED BOTANICAL DESCRIPTION

The aforementioned photographs, following observations and measurements describe plants grown during the winter and spring in 24-cm containers in an outdoor nursery in Higashiomi, Shiga, Japan and under cultural practices typical of commercial *Senecio* production. During the production of the plants, day temperatures averaged 10° C. and night temperatures averaged 5° C. Measurements and numerical values represent averages for typical flowering plants. Plants were six months old when the photographs and the detailed description were taken. In the following description, color references are made to The Royal Horticultural Society Colour Chart, 2015 Edition, except where general terms of ordinary dictionary significance are used.

Botanical classification: *Senecio cruentus* 'Sunsenehaha'.

Parentage:

*Female, or seed, parent.*—Proprietary selection of *Senecio cruentus* identified as code number 326, not patented.

*Male, or pollen, parent.*—Proprietary selection of *Senecio cruentus* identified as code number KW74, not patented.

Propagation:

*Type.*—Terminal vegetative cuttings.

*Time to initiate roots, summer and winter.*—About one week at temperatures about 18° C. to 20° C.

*Time to produce a rooted young plant, summer and winter.*—About four weeks at temperatures about 18° C. to 20° C.

*Root description.*—Fine, fibrous; typically white in color, actual color of the roots is dependent on substrate composition, water quality, fertilizer type and formulation, substrate temperature and physiological age of roots.

*Rooting habit.*—Freely branching.

Plant description:

*Plant form and growth habit.*—Upright and uniformly mounded plant habit; daisy-type inflorescences positioned above the foliar plane; vigorous growth habit; freely branching habit with about eight primary lateral branches with numerous secondary branches.

*Plant height.*—About 15 cm.

*Plant diameter.*—About 41 cm.

*Lateral branches.*—Length: About 12.5 cm. Diameter: About 3.6 mm. Internode length: About 1.5 cm. Strength: Strong. Aspect: Mostly upright. Texture: Sparsely pubescent. Color: Close to 144B.

*Leaf description.*—Arrangement: Alternate, simple. Length: About 6.5 cm. Width: About 7.4 cm. Shape: Cordate. Apex: Acute. Base: Cordate. Margin: Crenate to serrate with relatively shallow lobes; slightly undulate. Texture, upper surface: Sparsely pubescent. Texture, lower surface: Densely pubescent. Venation pattern: Pinnate; reticulate. Color: Developing leaves, upper surface: Close to 137B. Developing leaves, lower surface: Close to 191A. Fully expanded leaves, upper surface: Close to 137A; venation, close to 145B. Fully expanded leaves, lower surface: Close to 191A; venation, close to 145C. Leaf petioles: Length: About 6.5 cm. Diameter: About 3.2 mm. Texture, upper and lower surfaces: Pubescent. Color, upper and lower surfaces: Close to between 145C and 144B.

Inflorescence description:

*Appearance.*—Daisy-type inflorescences with elliptic-shaped ray florets; inflorescences arising from upper leaf axils and positioned above the foliar plane on strong peduncles; disc and ray florets developing acropetally on a capitulum; inflorescences face mostly upright to outwardly; freely flowering habit with about 59 inflorescences developing per plant.

*Fragrance.*—None detected.

*Natural flowering season.*—Plants of the new *Senecio* begin flowering about 22 weeks after planting; plants flower continuously from winter to late spring in Japan.

*Inflorescence longevity.*—Inflorescences last about two weeks on the plant; inflorescences persistent.

*Inflorescence buds.*—Height: About 1.6 cm. Diameter: About 8.7 mm. Shape: Globose. Color: Close to 83B.

*Inflorescence size.*—Diameter: About 5.4 cm. Depth (height): About 1.1 cm. Disc diameter: About 1.4 cm.

*Receptacles.*—Diameter: About 7.4 mm. Height: About 2.3 mm. Color: Close to 144C.

*Ray florets.*—Quantity and arrangement: About 14 to 17 per inflorescence arranged in a single whorl. Length: About 2.1 cm. Width: About 7.3 mm. Shape: Elliptic. Apex: Rounded. Base: Acute. Margin: Entire, not undulate. Aspect: Initially upright, then horizontal; flat. Texture, upper and lower surfaces: Shallowly ridged, glabrous. Color: When opening, upper surface: Close to N89A. When opening, lower surface: Close to N82A and N81A with stripes, close to N82D. Fully opened, upper surface: Close to N89B and N89C; color does not change with development. Fully opened, lower surface: Close to N81A, N82D and 85D.

*Disc florets.*—Quantity per inflorescence: About 98. Length: About 7.2 mm. Diameter, at apex: About 2.3 mm. Diameter, at base: About 1.5 mm. Shape: Tubular; apex dentate, five-pointed. Texture: Smooth, glabrous. Color, immature: Close to N92C. Color, mature: Close to 83A.

*Phyllaries.*—Quantity and arrangement: About 20 per inflorescence arranged in a single whorl. Length: About 6.5 mm. Width: About 1.9 mm. Shape: Lanceolate. Apex: Narrowly acute. Base: Fused. Margin: Entire. Texture, upper and lower surfaces: Smooth, glabrous. Color, upper surface: Close to 143A. Color, lower surface: Close to 139B.

*Peduncles.*—Length: About 9.1 cm. Diameter: About 1.5 mm. Strength: Strong. Aspect: Mostly upright. Texture: Sparsely pubescent. Color: Distally, close to NN137A; proximally, close to 146B.

*Reproductive organs.*—Androecium: Present on disc florets only. Filament length: About 0.7 mm. Filament color: Close to 155C. Anther size: About 1.9 mm by 0.4 mm. Anther shape: Narrowly ellipsoidal. Anther color: Close to N186B. Pollen amount: Moderate. Pollen color: Close to 6A. Gynoecium: Present on both ray and disc florets. Pistil length: About 8.8 mm. Stigma shape: Bi-parted. Stigma color: Close to 83A. Style color: Close to 145D. Ovary color: Close to 145D.

*Seeds and fruits.*—To date, seed and fruit development have not been observed on plants of the new *Senecio*.

Pathogen & pest resistance: To date, plants of the new *Senecio* have not been observed to be resistant to pathogens and pests common to *Senecio* plants.

Temperature tolerance: Plants of the new *Senecio* have been observed to tolerate temperatures ranging from about 0° C. to about 30° C.

It is claimed:

1. A new and distinct *Senecio* plant named 'Sunsenehaha' as illustrated and described.

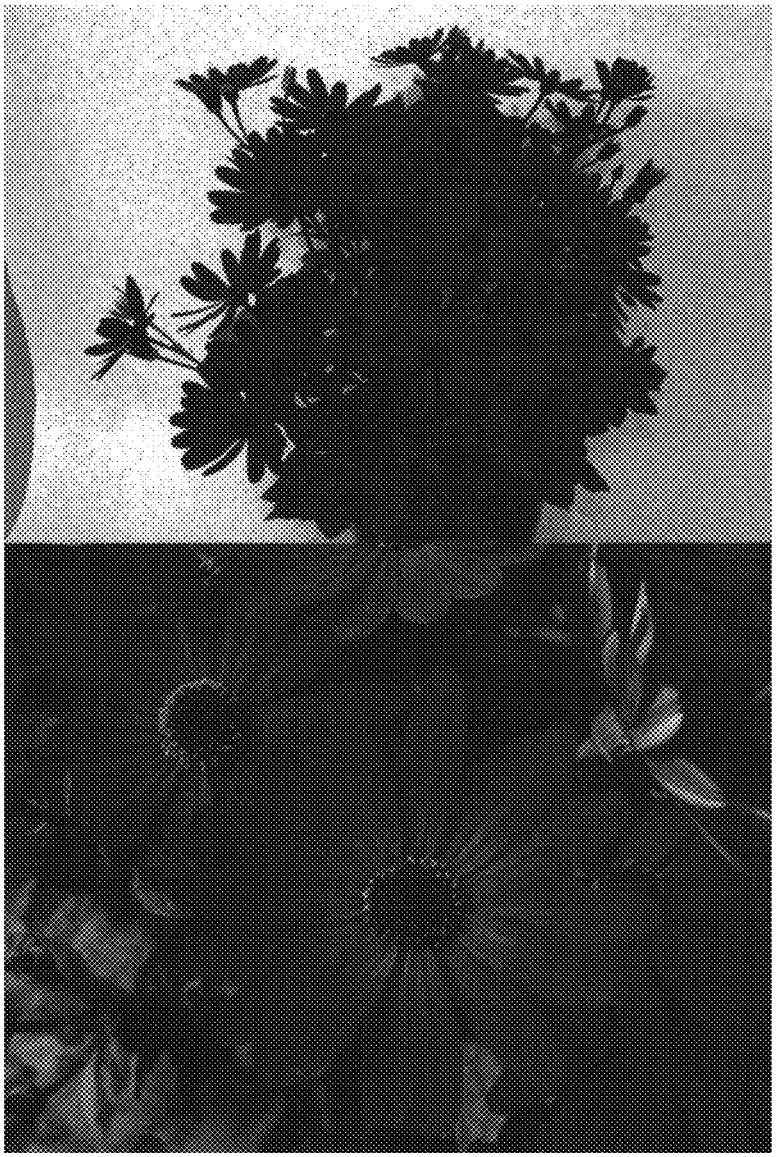

* * * * *